United States Patent
Bowman et al.

(10) Patent No.: US 8,167,832 B2
(45) Date of Patent: May 1, 2012

(54) AMBULATORY INFUSION DEVICES AND METHODS INCLUDING OCCLUSION MONITORING

(75) Inventors: Sam W. Bowman, Valencia, CA (US); Scott R. Gibson, Granada Hills, CA (US); Richard E. Purvis, Pasadena, CA (US); Brian Michael Shelton, Northridge, CA (US); Lawrence Eric Ong, Beverly Hills, CA (US); John Paul D'Brot, Santa Clarita, CA (US)

(73) Assignee: The Alfred E. Mann Foundation For Scientific Research, Santa Clarita, CA (US)

( * ) Notice: Subject to any disclaimer, the term of this patent is extended or adjusted under 35 U.S.C. 154(b) by 962 days.

(21) Appl. No.: 11/608,823

(22) Filed: Dec. 9, 2006

(65) Prior Publication Data

US 2008/0139996 A1    Jun. 12, 2008

(51) Int. Cl.
    *A61M 31/00*    (2006.01)
    *A61M 37/00*    (2006.01)
    *A61K 9/22*     (2006.01)
(52) U.S. Cl. .................... 604/65; 604/93.01; 604/890.1
(58) Field of Classification Search .............. 604/65, 604/502, 890.1, 151, 891.1, 505, 93.01, 288.01, 604/503
See application file for complete search history.

(56) References Cited

U.S. PATENT DOCUMENTS

| 3,926,056 A * | 12/1975 | Brown ........................... 73/753 |
| 4,013,074 A | 3/1977 | Siposs |
| 4,530,696 A | 7/1985 | Bisera et al. |
| 4,557,726 A | 12/1985 | Reinicke |
| 4,636,150 A | 1/1987 | Falk et al. |
| 4,690,673 A | 9/1987 | Bloomquist |
| 4,714,462 A | 12/1987 | DiDomenico |
| 4,718,893 A | 1/1988 | Dorman et al. |
| 5,006,997 A | 4/1991 | Reich |
| 5,190,522 A | 3/1993 | Wojcicki et al. |
| 5,695,473 A * | 12/1997 | Olsen ............................ 604/153 |
| 5,785,681 A | 7/1998 | Indravudh |
| 5,935,106 A * | 8/1999 | Olsen ............................ 604/153 |
| 5,989,222 A * | 11/1999 | Cole et al. ..................... 604/151 |
| 6,231,560 B1 * | 5/2001 | Bui et al. ....................... 604/500 |
| 6,354,999 B1 * | 3/2002 | Dgany et al. .................. 600/486 |
| 6,423,029 B1 | 7/2002 | Elsberry |
| 6,595,756 B2 | 7/2003 | Gray et al. |
| 6,620,151 B2 | 9/2003 | Blischak et al. |
| 7,022,116 B2 | 4/2006 | Morris |
| 7,054,782 B2 | 5/2006 | Hartlaub |
| 2004/0260229 A1 | 12/2004 | Meir |
| 2005/0038360 A1 * | 2/2005 | Shertukde et al. .......... 600/586 |
| 2005/0075624 A1 | 4/2005 | Miesel |
| 2005/0090799 A1 * | 4/2005 | Morris ............................ 604/500 |
| 2008/0021395 A1 * | 1/2008 | Yodfat et al. .................. 604/151 |

FOREIGN PATENT DOCUMENTS

| DE | 19642234 C1 | 4/1998 |
| WO | WO-96/27398 A1 | 9/1996 |
| WO | WO-99/55225 A1 | 11/1999 |
| WO | WO-2006/127508 A2 | 11/2006 |

* cited by examiner

Primary Examiner — Nicholas Lucchesi
Assistant Examiner — Rebecca E Eisenberg
(74) Attorney, Agent, or Firm — Henricks, Slavin & Holmes LLP

(57) ABSTRACT

Infusion devices with blockage detection capability and methods of monitoring infusion devices. High resolution pressure sensing and/or the sensing of a reflected pressure event may be used to detect a blockage.

29 Claims, 6 Drawing Sheets

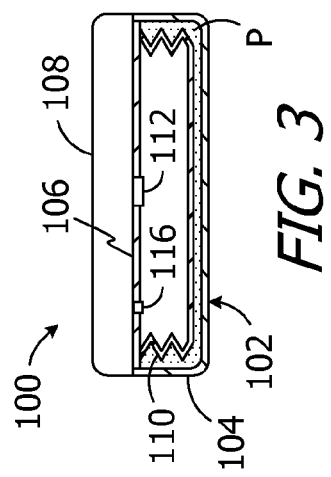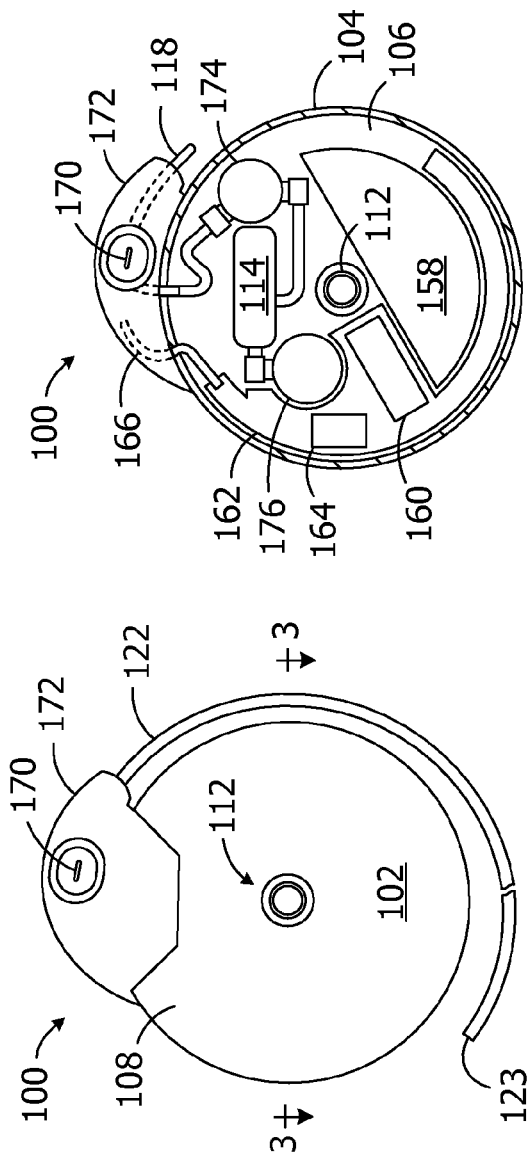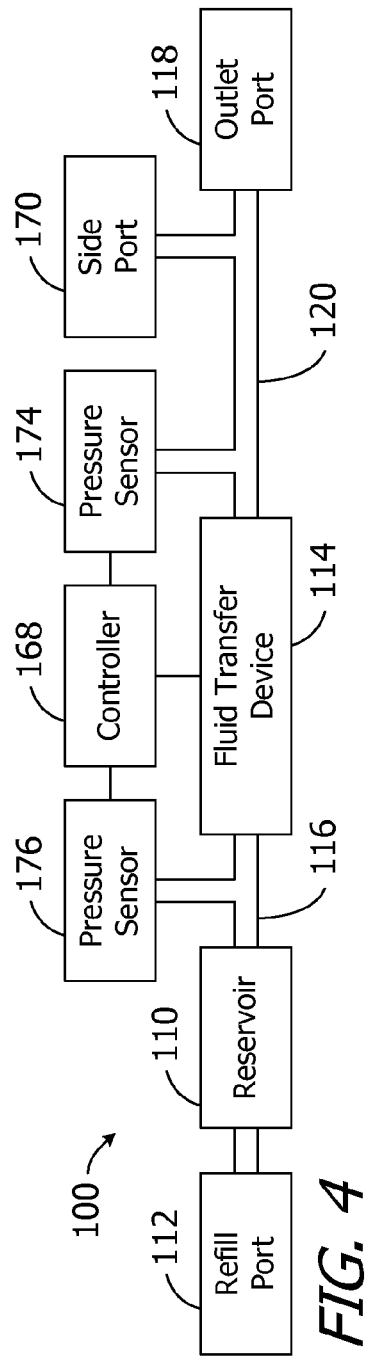

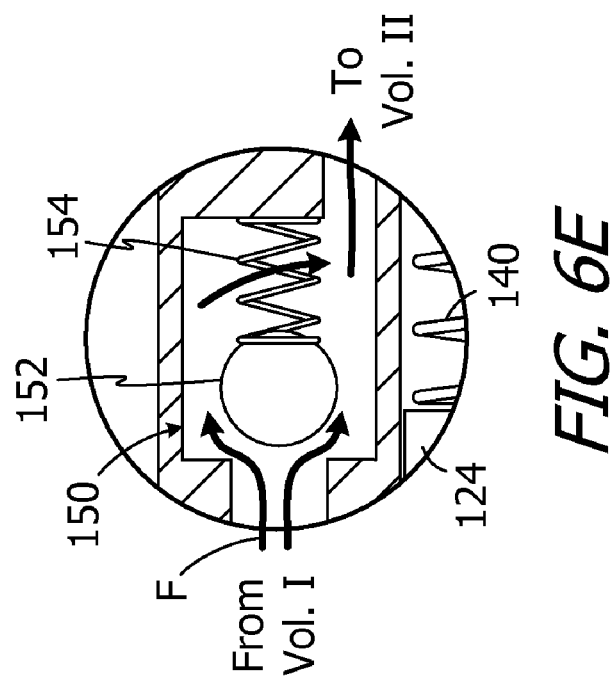
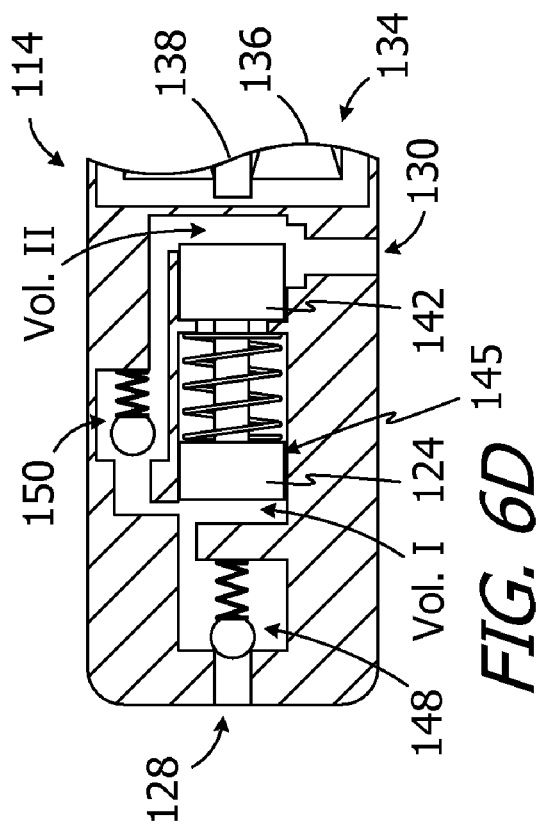

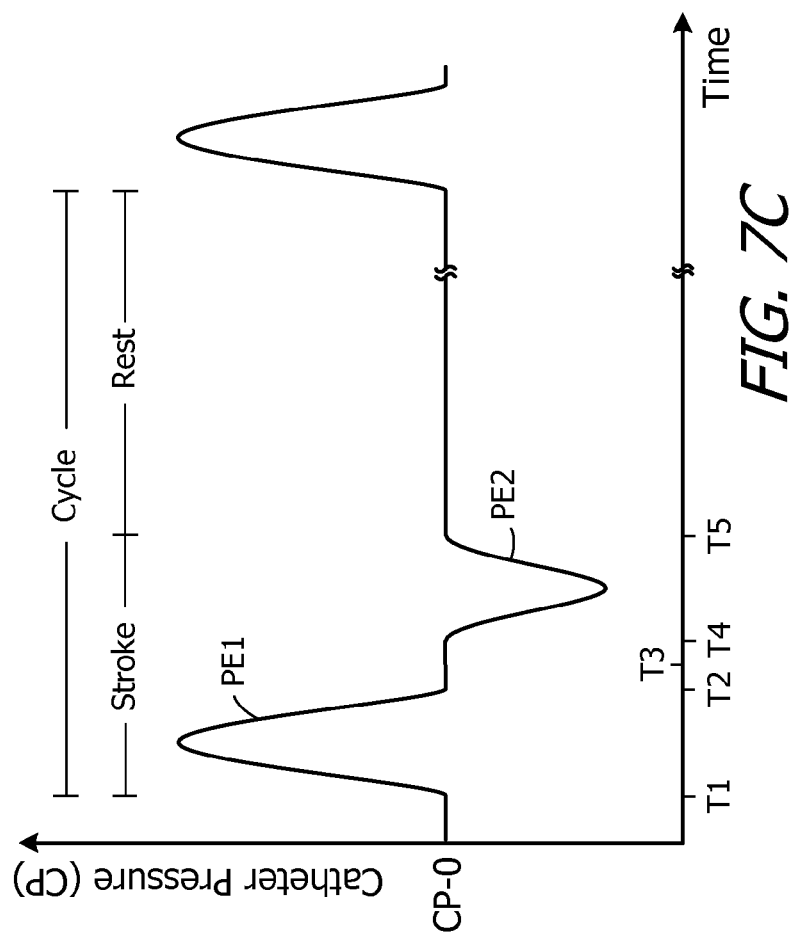
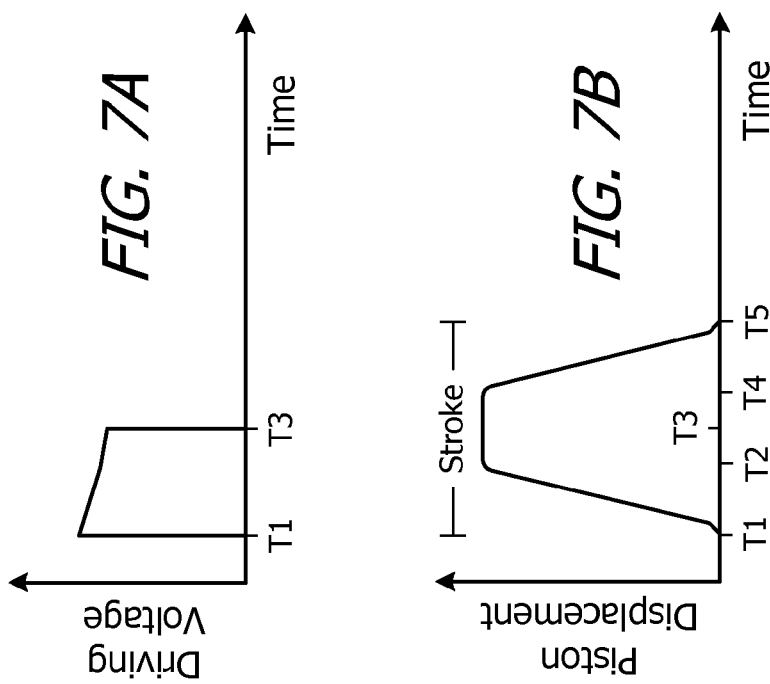
FIG. 7C
FIG. 7A
FIG. 7B

AMBULATORY INFUSION DEVICES AND METHODS INCLUDING OCCLUSION MONITORING

BACKGROUND OF THE INVENTIONS

1. Field of Inventions

The present inventions relate generally to ambulatory infusion devices.

2. Description of the Related Art

Ambulatory infusion devices, such as implantable infusion devices and externally carried infusion devices, have been used to provide a patient with a medication or other substance (collectively "infusible substance") and frequently include a reservoir and a pump. The reservoir is used to store the infusible substance and, in some instances, implantable infusion devices are provided with a fill port that allows the reservoir to be transcutaneously filled (and/or re-filled) with a hypodermic needle. The reservoir is coupled to the pump, which is in turn connected to an outlet port. A catheter, which has an outlet at the target body region, may be connected to the outlet port. As such, infusible the reservoir may be transferred from the reservoir to the target body region by way of the pump and catheter.

There are a number of blockage-related issues that can prevent an ambulatory infusion device from functioning properly. Catheters, for example, may become partially or completely blocked by the formation of tissue at the catheter outlet. Catheters may also develop kinks that can partially or completely block fluid flow. Partial blockages can prevent the patient from receiving the intended dosage of the infusible substance, while complete blockages will prevent any of the infusible substance from reaching the patient. The present inventors have determined that conventional methods of the detecting complete and partial blockages are susceptible to improvement.

SUMMARY OF THE INVENTIONS

The present apparatus and methods employ pressure measurements to identify complete and partial blockages. For example, the present apparatus and methods may employ high resolution sampling of sensed pressure to identify a blockage based on a reflected pressure event and/or a change in ambient pressure. Such apparatus and methods allow blockages to be identified far more rapidly than conventional apparatus and methods. Such apparatus and methods also facilitate the identification of the location of the blockages.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

FIG. 1 is a plan view of an implantable infusion device in accordance with one embodiment of a present invention.

FIG. 2 is a plan view of the implantable infusion device illustrated in FIG. 1 with the cover removed.

FIG. 3 is a partial section view taken along line 3-3 in FIG. 1.

FIG. 4 is a block diagram of the implantable infusion device illustrated in FIGS. 1-3.

FIGS. 6A, 6B and 6D are section views showing the pump illustrated in FIG. 5 in various states.

FIG. 6E is an enlarged view of a portion of FIG. 6D.

FIGS. 7A-7C are graphs illustrating various operational aspects of an infusion device.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions. The present inventions have application in a wide variety of infusion devices. One example of such a device is an implantable infusion device, for purposes of illustration, and the present inventions are discussed in the context of implantable infusion devices. The present inventions are not, however, limited to implantable infusion device and are instead also applicable to other infusion devices that currently exist, or are yet to be developed. For example, the present inventions are applicable to externally carried infusion devices.

Figure 5:
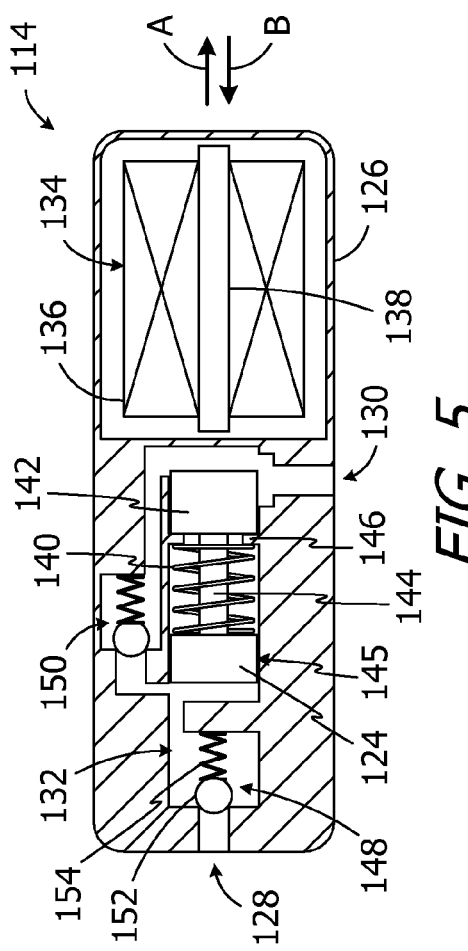
FIG. 5 is a section view of a pump in accordance with one example of a present invention.

One example of an ambulatory infusion device in accordance with a present invention is the implantable infusion device generally represented by reference numeral 100 in FIGS. 1-4. The exemplary infusion device 100 includes a housing 102 (e.g. a titanium housing) with a bottom portion 104, an internal wall 106, and a cover 108. An infusible substance (e.g. medication) may be stored in a reservoir 110 that is located within the housing bottom portion 104. The reservoir 110 may be replenished by way of a refill port 112 that extends from the reservoir, through the internal wall 106, to the cover 108. A hypodermic needle (not shown), which is configured to be pushed through the refill port 112, may be used to replenish the reservoir 110. The inlet of a fluid transfer device 114 is coupled to the interior of the reservoir 100 by a passageway 116, while the outlet of the fluid transfer device is coupled to an outlet port 118 by a passageway 120. Operation of the fluid transfer device 114, which is discussed in greater detail below with reference to FIGS. 5-6E, causes infusible substance to move from the reservoir 110 to the outlet port 118. A catheter 122 may be connected to the outlet port 118 so that the infusible substance passing through the outlet port will be delivered to a target body region in spaced relation to the infusion device 100 by way of the outlet 123 at the end of the catheter.

A wide variety of reservoirs may be employed. In the illustrated embodiment, the reservoir 110 is in the form of a titanium bellows that is positioned within a sealed volume defined by the housing bottom portion 104 and internal wall 106. The remainder of the sealed volume is occupied by propellant P, which may be used to exert negative pressure on the reservoir 110. Other reservoirs that may employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure which is always negative with respect to the ambient pressure.

Although the present inventions are not limited to any particular type of fluid transfer device, the exemplary fluid transfer device 114 is a electromagnet pump and an operation of the electromagnet pump is referred to herein as a stroke. To that end, and referring to FIG. 5, the exemplary fluid transfer device 114 includes a piston 124 that is located within a pump housing 126. Fluid from the reservoir 110 is drawn into the pump inlet 128 in response to movement of the piston 124 in the direction of arrow A during the first portion of the pump stroke, and is driven out of the pump outlet 130 in response to movement of the piston in the direction of arrow B during the second portion of the pump stroke. The pump inlet 128 and outlet 130 are connected to one another by a flow path 132. The piston 124 is driven back and forth by an electromechanical actuation system that includes an electromagnet 134, which consists of a coil 136 and a core 138, a spring 140, and a pole button 142. The pole button 142 is formed from a magnetic material, such as magnetic steel, and is connected to the piston 124 by a shaft 144. The piston 124, pole button 142 and shaft 144 form a unit that is referred to herein as the piston assembly 145. The spring 140, which is positioned about the shaft 144, is secured to the piston 124 and to a fixed mounting structure 146 on the housing 126.

The exemplary fluid transfer device 114 is also provided with a main check valve 148, which is associated with the inlet 128, and a bypass valve 150, which is located within the flow path 132 between the piston 124 and the outlet 130. The exemplary valves 148 and 150 are biased to the closed position illustrated in FIG. 5, and each include a ball 152 and a biasing spring 154. Other suitable valves include plunger valves.

Figure 6A:
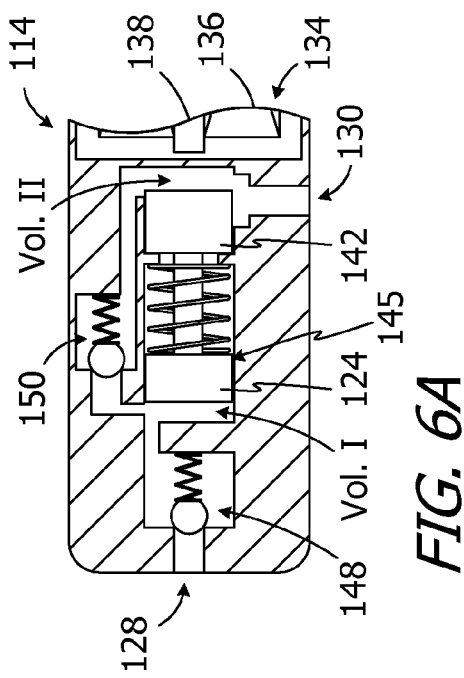
Figure 6C:
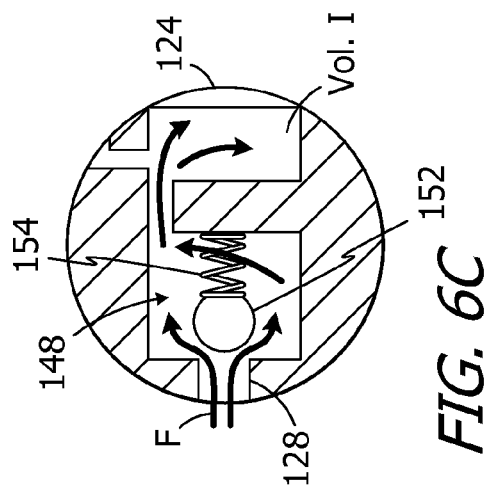
FIG. 6C is an enlarged view of a portion of FIG. 6B.

The exemplary fluid transfer device 114 operates in the manner illustrated FIGS. 6A-6E. Referring first to FIG. 6A, the fluid transfer device 114 is shown in the "rest" state. The piston assembly 145 is in the rest position, the electromagnet 134 is not energized, and the valves 148 and 150 are both closed. It should also be noted here that there are two volumes within the flow path 132, i.e. Vol. I and Vol. II, that increase and decrease in volume as a result of movement of the piston 124 and pole button 142. Vol. I is in its smaller state and Vol. II is in its larger state when the piston assembly 145 is in the rest position.

Under normal operating conditions, there will be no flow through the fluid transfer device 114 when the fluid transfer device is in the rest state and the valves 148 and 150 are closed. Although sufficient pressure at the pump inlet 128 could result in the flow through the fluid transfer device 114 while the fluid transfer device is in the rest state illustrated in FIG. 6A, the likelihood that this could occur is greatly reduced by maintaining the reservoir 110 at a relatively low pressure. The orientation of valve 150 prevents backflow that could result from pressure at the pump outlet 130.

Figure 6B:
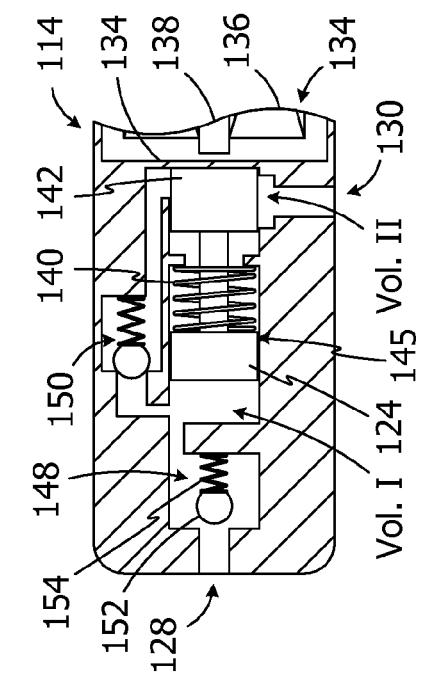

The exemplary fluid transfer device 114 is actuated by connecting the coil 136 in the electromagnet 134 to an energy source (e.g. one or more capacitors that are being fired). The resulting magnetic field is directed through the core 138 and into, as well as through, the pole button 142. The pole button 142 is attracted to the core 138 by the magnetic field. The intensity of the magnetic field grows as current continues to flow through the coil 136. When the intensity reaches a level sufficient to overcome the biasing force of the spring 140, the pole button 142 will be pulled rapidly in the direction of arrow A (FIG. 5) until the pole button reaches the wall 156, as shown in FIG. 6B. The piston 124 will move with pole button 142 and compress the spring 140. Movement of the piston assembly 145 from the position illustrated in FIG. 6A to the position illustrated in FIG. 6B results in the Vol. I expanding to its larger state, which results in a decrease in pressure within Vol. I, and Vol. II contracting to its smaller state, which results in an increase in pressure within Vol. II. This portion of the pump stroke takes about 1.0 milliseconds.

The coil will continue to be energized for about 2.5 milliseconds in order to hold the piston assembly 145 in the location illustrated in FIG. 6B during the intermediate portion of the pump stroke. During this time, the reduction in pressure within Vol. I will open the main check valve 148 by overcoming the biasing force of the spring 154 and move the ball 152 away from the pump inlet 128. As illustrated for example in FIG. 6C, the reduction in pressure within Vol. I, coupled with movement of the ball 152 away from the pump inlet 128, results in fluid F (such as medication or other infusible substance) flowing into Vol. I. The main check valve 148 will close, due to the force exerted by spring 154 on the ball 152, once the pressure within Vol. I is equal to pressure at the pump inlet 128. However, because the coil 136 continues to be energized, the piston assembly 145 will remain in the position illustrated in FIG. 6B as fluid flows into Vol. I and the main check valve 148 closes.

Immediately after the main check valve 148 closes, the coil 136 will be disconnected from the energy source and the magnetic field established by the electromagnet 134 will decay until it can no longer overcome the force exerted on the piston 124 by the spring 140. The piston assembly 145 will then move back to the position illustrated in FIG. 6A. As a result, Vol. I will decrease back to its smaller state, which results in an increase in pressure within Vol. I, and Vol. II expand to its larger state, which results in a decrease in pressure within Vol. II. During this time, the increase in pressure within Vol. I will open the bypass valve 150 by overcoming the biasing force of the spring 154 and moving the ball 152. Turning FIG. 6E, the increase in pressure within Vol. I, coupled with movement of the ball 152 away from the pump inlet 128 and the decrease in pressure within Vol. II, results in the fluid F flowing from Vol. I though Vol. II and out of the pump outlet 130. About 0.25 µL/stroke will pass through the pump outlet 130 in the illustrated embodiment. The flow of fluid will cause the pressure within Vols. I and 11 is equalize. At this point, the bypass valve 150 will close, due to the force exerted by spring 154 on the ball 152, thereby returning the exemplary fluid transfer device 114 to the rest state illustrated in FIG. 6A. This portion of the pump stroke takes about 0.1 milliseconds, although it may vary.

The present inventions are not limited to electromagnet pumps and may include other types of fluid transfer devices. Such devices include, but are not limited to, solenoid pumps, piezo pumps, and any other mechanical or electromechanical pulsatile pump. In the exemplary context of implantable drug delivery devices, and although the volume/stroke magnitude may be increased in certain situations, the fluid transfer devices will typically deliver about 1 milliliter/stroke or less. Additionally, although the exemplary fluid transfer device 114 is provided with internal valves, valves may also be provided as separate structural elements that are positioned upstream of and/or downstream from the associated fluid transfer device.

Energy for the fluid transfer device 114, as well for other aspects of the exemplary infusion device 100, is provided by the battery 158 illustrated in FIG. 2. In the specific case of the fluid transfer device 114, the battery 158 is used to charge one or more capacitors 160, and is not directly connected to the fluid transfer device itself. The capacitor(s) 160 are connected to the coil 136 of the fluid transfer device 114, and disconnected from the battery 158, when the coil 136 is being energized, and are disconnected from the coil and connected to the battery when the capacitor(s) are being recharged and/or when the fluid transfer device is at rest. The capacitor(s) 160 are carried on a board 162. A communication device 164, which is connected to an antenna 166, is carried on the same side of the board 162 as the capacitor(s) 160. The exemplary communication device 164 is an RF communication device. Other suitable communication devices include, but are not limited to, oscillating magnetic field communication devices, static magnetic field communication devices, optical communication devices, ultrasound communication devices and direct electrical communication devices.

A controller 168, such as a microprocessor, microcontroller or other control circuitry, is carried on the other side of the board 162. The controller controls the operations of the infusion device 100 in accordance with instructions stored in memory (not shown) and/or provided by and external device by way of the communication device 164. For example, the controller 168 may be used to control the fluid transfer device 114 to supply fluid to the patient in accordance with, for example, a stored basal delivery schedule, or a bolus delivery request.

Referring to FIGS. 2 and 4, the exemplary infusion device 100 is also provided with a side port 170 that is connected to the passageway 120 between the outlet of the fluid transfer device 114 and the outlet port 118. The side port 170 facilitates access to an implanted catheter 122, typically by way of a hypodermic needle. For example, the side port 170 allows clinicians to push fluid into the catheter 122 and/or draw fluid from the catheter.

The outlet port 118, a portion of the passageway 120, the antenna 166 and the side port 170 are carried by a header assembly 172. The header assembly 172 is a molded, plastic structure that is secured to the housing 102. The housing 102 includes a small aperture through which portions of the passageway 120 are connected to one another, and a small aperture through which the antenna 166 is connected to the board 162.

The exemplary infusion device 100 illustrated in FIGS. 1-4 also includes a pressure sensor 174 that is connected to the passageway 120 between the outlet of the fluid transfer device 114 and the outlet port 118. As such, the pressure sensor 174 senses the pressure at the outlet port 118 which, in the illustrated embodiment, is also the pressure within the catheter 122. Another pressure sensor 176 is connected to the passageway 116 between the reservoir 110 and the inlet of the fluid transfer device 114. The pressure sensor 176 senses the pressure at the inlet of the fluid transfer device 114 and may be used to measure the reservoir pressure. The pressure sensors 174 and 176, which are connected to the controller 168, may also be used to measure the pressure differential across the fluid transfer device 114.

The pressure measurements from the pressure sensor 174 and/or the pressure sensor 176 may be used to analyze a variety of aspects of the operation exemplary infusion device 100. For example, pressure measurements may be used to determine whether or not there is a complete or partial blockage in the catheter 122. In particular, high resolution sampling may be used to sample the pressure measured by the sensor(s) many times during a pump cycle and/or a pump stroke. High resolution sampling involves the controller 168 sampling at a frequency that is, at a bare minimum, twice the frequency of the fluid path. A minimum of ten times the frequency of the fluid path may be used to better insure that the reflections are observed. Accordingly, in the illustrated embodiment where the frequency of the fluid path is about 40 kHz, the high resolution sampling would involve the controller 168 taking at least about 400 pressure measurement samples per millisecond. A suitable range would be about 400 to 10,000 or more pressure measurement samples per millisecond. To put that range into perspective, a pump stroke in the exemplary fluid transfer device 114 may take about 10 milliseconds and a pump cycle may take about 1 second, i.e. a stroke during the first 10 milliseconds of the cycle and rest during the remaining 990 milliseconds. In one exemplary mode of operation, there will be 1-4 strokes at the beginning of each minute and the pump will remain at rest for the remainder of the minute. The analysis may, for example, be based on high resolution sampling of pressure measurements taken over all or part of a single pump stroke and/or all or part of a single pump cycle. In addition, high resolution sampling of pressure measurements taken over a few additional single pump strokes and/or additional single pump cycles may be used to confirm the results of the initial measurements.

In order to facilitate understanding of the pressure measurements that are indicative of a complete or partial blockage in the catheter 122, the operation of a properly functioning infusion device 100, in combination with a catheter 122 that is not blocked, is graphically illustrated in FIGS. 7A-7C. FIG. 7A-7C illustrate, as a function of time, the driving voltage applied to the electromagnet coil 136, the displacement of the piston 124, and a high resolution sampling of the pressure sensed at pressure sensor 174 (i.e. the sensor between the outlet of the fluid transfer device 114 and the catheter 122) by the controller 168. Prior to Time T1, which represents the beginning of pump cycle and pump stroke, the ambient catheter pressure CP is measured by the pressure sensor 174. This pre-stroke pressure is represented by CP-0 in FIG. 7C. A driving voltage is applied to the coil 136 by the capacitor(s) 160 at time T1. The resulting magnetic field causes the piston assembly 145 to move from the position illustrated in FIG. 6A to the position illustrated in FIG. 6B. This movement, which occurs between time T1 and time T2, displaces the fluid in Vol. II through the pump outlet 130 which, in turn, creates a positive pressure event PE1 (FIG. 7C) that passes, and is sensed by, the pressure sensor 174. The pressure event PE1 will travel through the catheter 122 and through the unblocked outlet 123.

The driving voltage, which decays slightly during the intermediate portion of the pump stroke where the piston assembly 145 is held in the position illustrated in FIG. 6B against the force of the spring 140, is removed at time T3. The pressure sensed by pressure sensor 174, i.e. the ambient catheter pressure CP, is the same during this portion of the pump stroke (CP-0) as it was prior to the pump stroke. After sufficient weakening of the magnetic field, the spring 142 will push the piston assembly 145 to the position illustrated in FIG. 6D. This movement, which occurs between time T4 and time T5 and defines the end of the pump stroke, causes Vol. II to increase. The increase in Vol. II results in a negative pressure event PE2 (FIG. 7C) that is also sensed by pressure sensor 174. It should be noted here that the pressure event PE2 is smaller in magnitude than pressure event PE1 because fluid from Vol. I enters Vol. II by way of the bypass valve 150 (FIGS. 6D and 6E) at this time. The ambient catheter pressure CP will again return to CP-0 and fluid transfer device 114 will remain at rest for the remainder of the cycle.

Figure 8:
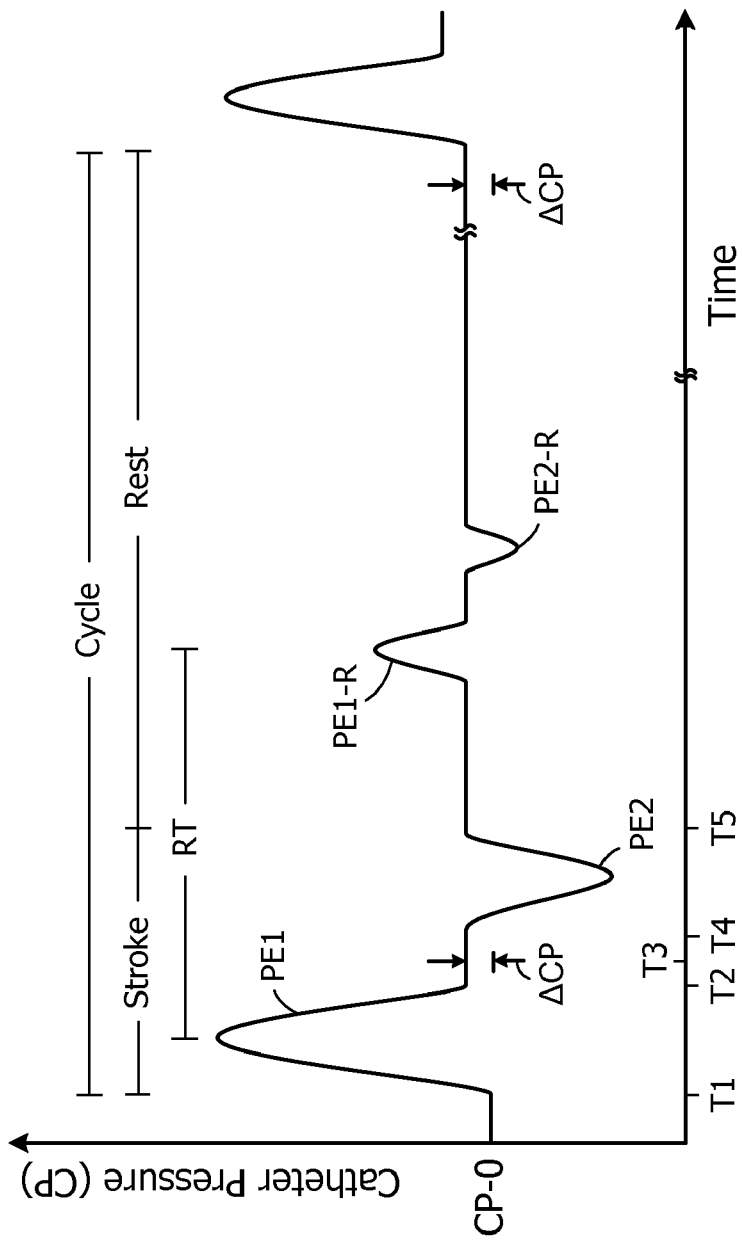
FIG. 8 is a graph illustrating pressure measurements taken by an infusion device during a single pump cycle.

FIG. 8 is also a graphical representation of the pressure sensed at pressure sensor 174 in the exemplary infusion device 100. The application of the driving voltage to the electromagnet coil 136 is the same as that shown in FIGS. 7A. Here, however, the outlet 123 at the end of the catheter 122 is completely blocked and the blockage creates a number of pressure related phenomena that are detectable through the use of high resolution sampling of pressure measurements that are taken during a pump stroke and/or during the rest period that accounts for the remainder of the associated pump cycle. In particular, the blockage reflects the pressure events PE1 and PE2 caused by the pump stroke back through the catheter to the pressure sensor 174. The reflections of pressure events are labeled PE1-R and PE2-R in FIG. 8. The blockage also causes the ambient pressure CP within the catheter 122 to increase during the first half of the pump stroke, i.e. as the piston assembly 145 moves from the position illustrated in FIG. 6A to the position illustrated in FIG. 6B and pushes fluid into the catheter that, due to the complete blockage, is unable to escape. The increase in ambient pressure within the catheter 122 is represented by ΔCP. The increase ΔCP in ambient catheter pressure CP, which also results in a pressure event PE2 that is smaller in magnitude than would be the case, is observable during the intermediate portion of the pump stroke as well as during the rest period subsequent to the pump stroke and prior to the next pump stroke.

Figure 9:
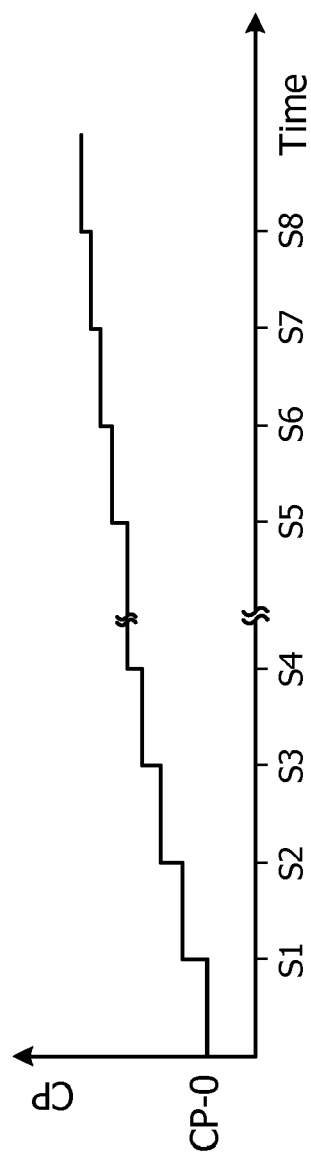
FIG. 9 is a graph illustrating pressure measurements taken by an infusion device over a plurality of pump cycles.

It should be noted here that, in the case of the complete blockage illustrated in FIG. 8, the increase ΔCP in the ambient catheter pressure CP will not substantially dissipate over time. During the second half of the pump stroke, i.e. as the piston assembly 145 moves from the position illustrated in FIG. 6B to the position illustrated in FIG. 6D, Vol. II will be refilled by fluid from Vol. I, and during the remainder of the pump cycle the bypass valve 150 will be closed. Thus, if the exemplary infusion device 100 were to continue to operate despite the fact that the complete blockage was identified by the controller 168 in the manner described below, the ambient pressure would continue to increase (or "accumulate") stroke after stroke in the manner illustrated in FIG. 9. The magnitude of pressure increase ΔCP will decrease with each stroke due to the build-up of fluid within the catheter 122, as illustrated by exemplary strokes S1-S8, until the "dead end" pressure is reached and no forward fluid delivery is accomplished.

As noted above, pressure measurements from pressure sensor 174 are sampled by the controller 168 at a high resolution rate prior to the pump stroke, during the pump stroke and during the remainder of the pump cycle. The controller 168 will, therefore, detect the presence of the reflections PE1-R and PE2-R of pressure events RPE1 and RPE2 and will interpret the reflections as being indicative of a catheter blockage. The controller 168 may also rely on the detection of the reflections PE1-R and PE2-R of pressure events PE1 and PE2 associated with subsequent pump strokes (e.g. 1-3 subsequent pump strokes) to confirm the initial blockage determination.

The controller 168 will also detect the fact that the increase ΔCP in the ambient catheter pressure CP did not substantially dissipate during the remainder of the pump cycle. The controller 168 will interpret the fact that the ambient catheter pressure increased during the first half of the pump stroke, and then did not substantially dissipate during the remainder of the pump cycle, as being indicative of a complete blockage.

The location of the blockage may be determined by the controller 168 based in part upon the amount of time that elapses between the sensing of the pressure event PE1 (or PE2) at the pressure sensor 174 and the subsequent sensing of the pressure event reflections PE1-R (or PE2-R) at the pressure sensor 174. This time period, which is referred to herein as the reflection time RT, represents the amount of time that it takes a pressure event to travel from the pressure senor 174 to the blockage and then back to the pressure sensor. The controller 168 may, for example, determine the reflection time RT based on the amount of time that elapses between the peak of the pressure event PE1 and the peak of the reflect PE1-R, as is illustrated in FIG. 8. The other bases for the location of the blockage determination are the length of the catheter 122, which is stored in memory, and the speed at which the pressure events travel through the infusible substance, which may be equated to the speed of sound through water or saline (e.g. about 1530 m/s) for purposes of a close approximation and also stored in memory. The total distance that the pressure event travels is equal to the product of the reflection time RT and the speed, and the distance to the blockage is one-half of the total distance. The distance to the blockage may be compared to the length of the catheter 122 to determine whether the blockage is located at the catheter outlet 123, or some location between the outlet port 118 and the catheter outlet. For example, if the measured reflection time RT equals 0.2 milliseconds, the controller 168 will determined that the pressure event traveled a total of 30 cm. The distance to the blockage is one-half of the total, or 15 cm. This distance is then compared to the length of the catheter 122. If the distance to the blockage is approximately equal to the length of the catheter, the controller 168 will determine that the blockage is located at the outlet 123, as is the case in the example illustrated in FIG. 8.

Figures 10, 11:
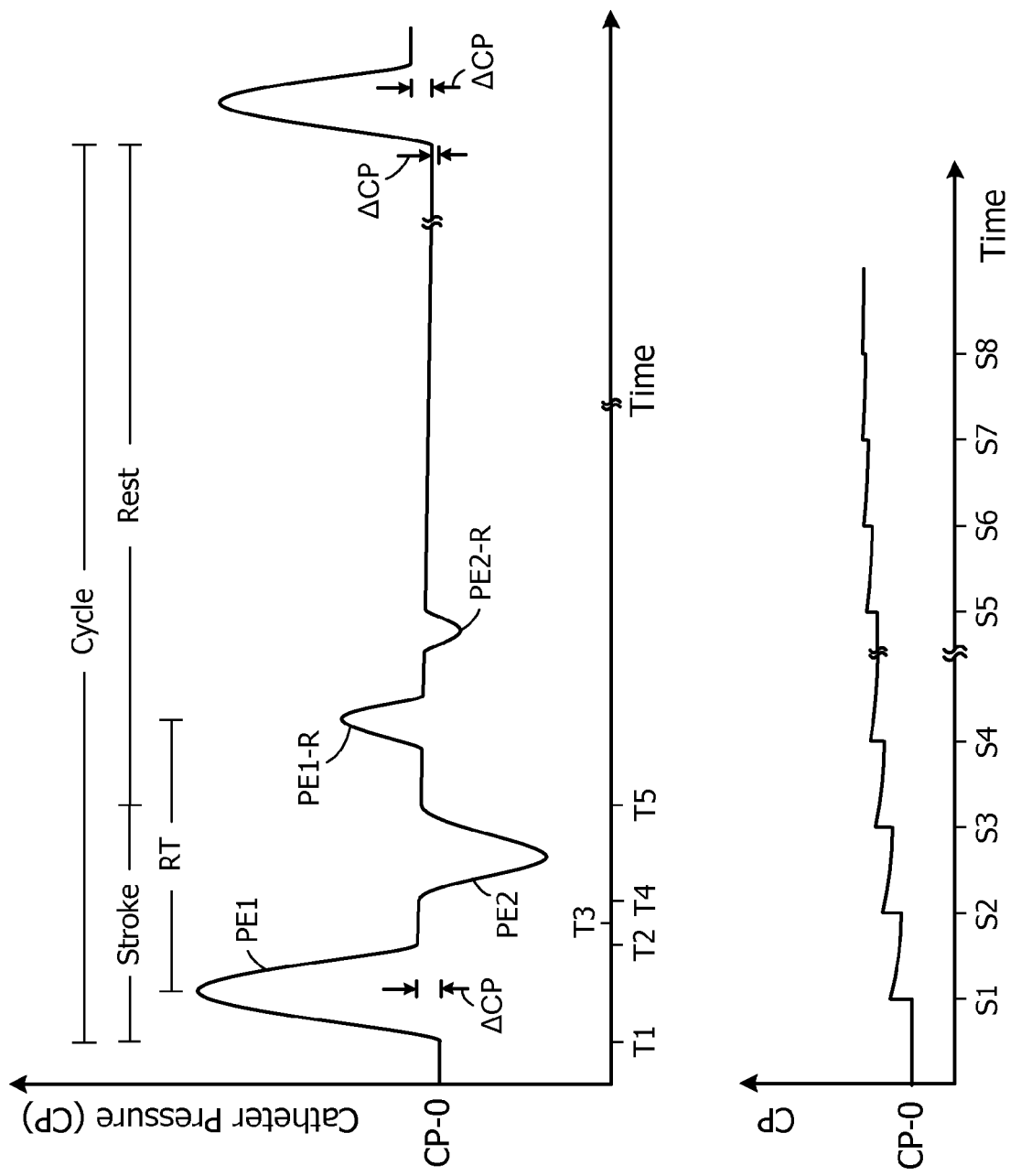
FIG. 10 is a graph illustrating pressure measurements taken by an infusion device during a single pump cycle.
FIG. 11 is a graph illustrating pressure measurements taken by an infusion device over a plurality of pump cycles.

FIG. 10 is also a graphical representation of the pressure sensed at pressure sensor 174 in the exemplary infusion device 100. The application of the driving voltage to the electromagnet coil 136 is the same as that shown in FIG. 7A. Here, however, there is a kink or other partial blockage within the catheter 122 and the partial blockage is located between the outlet port 118 and the outlet 123. The blockage creates a number of pressure related phenomena that are detectable through the use of high resolution sampling of pressure measurements that are taken during a pump stroke and/or during the rest period that accounts for the remainder of the associated pump cycle. Much like the complete blockage, the partial blockage reflects the pressure events PE1 and PE2 caused by the pump stroke back through the catheter to the pressure sensor 174. The reflections of pressure events are labeled PE1-R and PE2-R in FIG. 10. The blockage also causes the ambient pressure CP within the catheter 122 to increase during the first half of the pump stroke, i.e. as the piston assembly 145 moves from the position illustrated in FIG. 6A to the position illustrated in FIG. 6B and pushes fluid into the catheter. The increase in ambient pressure within the catheter 122 is represented by ΔCP. The increase ΔCP in ambient catheter pressure CP, which also results in a pressure event PE2 that is smaller in magnitude than would be the case, is observable during the intermediate portion of the pump stroke as well as subsequent to the pump stroke.

Unlike a complete blockage (FIG. 8), the increase ΔCP in the ambient catheter pressure CP will dissipate over time and the dissipation will begin immediately after the first half of the pump stroke ends. The reduction in ambient catheter pressure CP is caused by fluid escaping through the open portion of the partially blocked region of the catheter. Thus, as illustrated in FIG. 10, the magnitude of ΔCP is greatest at the end of the first half of the pump stroke and is substantially smaller at the end of the pump cycle. Nevertheless, if the exemplary infusion device 100 were to continue to operate despite the fact that the partial blockage was identified by the controller 168 in the manner described below, the ambient pressure would continue to increase (or "accumulate") stroke after stroke in the manner illustrated in FIG. 11. The magnitude of pressure increase ΔCP will decrease with each stroke due to the build-up of fluid within the catheter 122, as illustrated by exemplary strokes S1-S8, until the "dead end" pressure is reached. It should also be noted that, unlike the complete block pressure accumulation illustrated in FIG. 9, the pressure accumulation illustrated in FIG. 11 includes pressure decrease between the strokes.

Pressure measurements from pressure sensor 174 are sampled by the controller 168 at a high resolution rate before the pump stroke, during the pump stroke and during the remainder of the pump cycle. The controller 168 will, therefore, detect the presence of the reflections PE1-R and PE2-R of pressure events RPE1 and RPE2 and will interpret the reflections as being indicative of a catheter blockage. Pressure measurements associated with subsequent pump strokes may be used to confirm the initial blockage determination. The controller 168 will also detect the fact that the increase ΔCP in the ambient catheter pressure CP dissipated during the remainder of the pump cycle. The controller 168 will interpret the fact that the ambient catheter pressure CP increased during the first half of the pump stroke, and then dissipated during the remainder of the pump cycle, as being indicative of a partial blockage.

The location of the blockage may be determined, as is described in greater detail above, based upon the reflection time RT, i.e. the amount of time that elapses between the sensing of the pressure event PE1 (or PE2) at the pressure sensor 174 and the subsequent sensing of the pressure event reflection PE1-R (or PE2-R) at the pressure sensor 174, the length of the catheter 122, and the speed at which the pressure events travel through the infusible substance. The blockage associated with FIG. 10 is located between the outlet port 118 and the catheter outlet 123. As such, the reflection time RT is less than that associated with a blockage at the catheter outlet 123. The calculated distance traveled by the pressure event reflection PE1-R (or PE2-R) will, therefore, be less than twice the length of the catheter 122. Based on this calculation, the controller 168 will determine that the blockage is located one-half of the distance traveled by the pressure event reflection PE1-R (or PE2-R) from the pressure sensor 174 and that this distance corresponds to a location other than the catheter outlet 123. Blockages between the outlet port 118 and the catheter outlet 123 are typically associated with kinks in the catheter 122.

The controller 168 may perform a variety of different functions in response to the detection of a blockage. For example, the controller 168 may actuate an audible alarm that is located within the housing 102 in order to alert the person in which the infusion device 100 is implanted. Different alarms may be used to represent complete and partial blockages. An audible alarm may also be used to advise the person that the blockage is no longer present. This may occur, for example, when the blockage is due to a kink caused by the movement and unkinking cause by subsequent movement. The controller 168 may cause the communication device 164 to transmit information about the blockage to an external device such as remote control, which may in turn provide audible or visual information about the blockage, or to a clinicians programming unit. Information about the blockage may also be stored in memory within the infusion device 100 so that it may be accessed later.

Referring again to FIG. 7C, there are a number of aspects of the high resolution pressure measurement illustrated therein that the controller 168 will use to determine that the catheter 122 is operating properly and is not completely or partially blocked. For example, there are no reflected pressure events that are indicative of a blockage. Although there may be some extremely small pressure event reflections that are related to circumstances other than blockages (e.g. a pressure event passing through the outlet port 118 or a bend in the catheter 122), such reflections will be so small in magnitude that they will not be observable or will be ignored when observed and sampled. The catheter pressure CP measured after the pump stroke is also the same as the catheter pressure CP-0 measured prior to the pump stroke. The lack of a change in catheter pressure is also indicative of a catheter that is not blocked.

The analysis of the pressure measurements described above in the context of FIGS. 7C-11 is a time domain analysis. It should be noted, however, that the present inventions are not limited to time domain analysis. Frequency domain analysis, where blockages are represented by changes in the components of the frequency spectrum, may also be employed.

Although the inventions disclosed herein have been described in terms of the preferred embodiments above, numerous modifications and/or additions to the above-described preferred embodiments would be readily apparent to one skilled in the art. By way of example, but not limitation, the present inventions have application in infusion devices that include multiple reservoirs and/or outlets. It is intended that the scope of the present inventions extend to all such modifications and/or additions and that the scope of the present inventions is limited solely by the claims set forth below.

We claim:

1. A method of monitoring an infusion device including a pump and an outlet, the method comprising the steps of:
   sensing pressure within a catheter connected to the outlet prior to a single pump stroke;
   sensing pressure within the catheter during the single pump stroke; and
   determining that the catheter is blocked in response to an increase in pressure within the catheter, as compared to the pressure within the catheter sensed prior to the single pump stroke, that is measured during the single pump stoke between positive and negative pressure events associated with the single pump stoke.

2. A method as claimed in claim 1, further comprising the steps of:
   sensing pressure within the catheter after the single pump stroke; and
   determining that the catheter is partially blocked in response to the pressure within catheter dissipating over time subsequent to the increase in pressure and prior to the next pump stroke.

3. A method as claimed in claim 1, further comprising the steps of:
   sensing pressure within the catheter after the single pump stroke; and
   determining that the catheter is completely blocked in response to the pressure within catheter remaining substantially constant subsequent to the increase in pressure and prior to the next pump stroke.

4. A method as claimed in claim 1, further comprising the steps of:
   taking high resolution samples of the pressure sensed during the single pump stroke.

5. A method as claimed in claim 1, wherein
   the pump comprises a piston pump with a piston; and
   the pump stroke is defined by a single cycle of back and forth movement of the piston that delivers about 1 milliliter or less of fluid.

6. A method as claimed in claim 1, wherein
   the single pump stroke occurs in response to a single actuation of the pump.

7. A method as claimed in claim 6, wherein
fluid is driven out of the pump and is drawn into the pump during the single pump stroke.

8. An infusion device, comprising:
an outlet port;
a fluid transfer device operably connected to the outlet port;
a fluid path defining a frequency;
a pressure sensor associated with the fluid path located between the fluid transfer device and the outlet port; and
means for taking samples of the pressure sensed by the pressure sensor at at least twice the frequency of the fluid path.

9. An infusion device as claimed in claim 8, further comprising:
a reservoir operably connected to the fluid transfer device.

10. An infusion device as claimed in claim 8, further comprising:
means for determining that a blockage is present in response to a sampled reflection of a pressure event.

11. An infusion device as claimed in claim 10, further comprising:
means for determining the location of the blockage.

12. An infusion device as claimed in claim 10, further comprising:
means for determining whether the blockage is a partial blockage or a complete blockage.

13. An infusion device as claimed in claim 8, further comprising:
means for determining that a blockage is present in response to a change in ambient catheter pressure resulting from a single pump stroke.

14. An infusion device as claimed in claim 8, wherein the samples are taken at at least ten times the frequency of the fluid path.

15. An infusion device, comprising:
an outlet port;
a fluid transfer device operably connected to the outlet port;
a pressure sensor located between the fluid transfer device and the outlet port; and
a controller that takes samples of the pressure sensed by the pressure sensor at a rate of at least about 400,000 samples/second.

16. An infusion device as claimed in claim 15, further comprising:
a reservoir operably connected to the fluid transfer device.

17. An infusion device as claimed in claim 15, wherein the controller is configured to identify a blockage in response to a sampled reflection of a pressure event.

18. An infusion device as claimed in claim 17, wherein the controller is configured to determine the location of the blockage.

19. An infusion device as claimed in claim 17, wherein the controller is configured to determine whether the blockage is a partial blockage or a complete blockage.

20. An infusion device as claimed in claim 15, wherein the controller is configured to identify a blockage in response to a change in ambient catheter pressure resulting from a single pump stroke.

21. An infusion device as claimed in claim 15, wherein the samples are taken at a rate of between about 400,000 samples/second and about 10,000,000 samples/second.

22. A method of monitoring an infusion device including an infusion device outlet and a piston pump, the piston pump including a piston that moves back and forth, a cycle of the back and forth movement defining a pump stroke that has a beginning and an end, the method comprising the steps of:
sensing pressure with a sensor located at a sensing location between the piston pump and a catheter outlet of a catheter connected to the infusion device outlet prior to the beginning of a single pump stroke of the piston pump;
sensing pressure with the sensor located at the sensing location during the single pump stroke of the piston pump; and
determining that the catheter is blocked in response to an increase in pressure at the sensing location, as compared to the pressure at the sensing location sensed prior to the beginning of the single pump stroke of the piston pump, that is measured after the beginning and prior to the end of the single pump stroke of the piston pump.

23. A method as claimed in claim 22, wherein
wherein the step of determining that the catheter is blocked comprises determining that the catheter is blocked in response to an increase in pressure at the sensing location, as compared to the pressure at the sensing location sensed prior to the beginning of the single pump stroke of the piston pump, that is measured at approximately the midpoint of the single pump stroke of the piston pump.

24. A method as claimed in claim 22, further comprising:
determining that the catheter is completely blocked in response to the pressure at the sensing location remaining substantially constant subsequent to the increase in pressure and prior to the next pump stroke of the piston pump.

25. A method as claimed in claim 22, further comprising:
determining that the catheter is partially blocked in response to the pressure at the sensing location dissipating over time subsequent to the increase in pressure and prior to the next pump stroke of the piston pump.

26. A method as claimed in claim 22, further comprising the steps of:
taking high resolution samples of the pressure sensed after the beginning and prior to the end of the single pump stroke of the piston pump.

27. A method as claimed in claim 22, wherein
the pump stroke is defined by a single cycle of back and forth movement of the piston that delivers about 1 milliliter or less of fluid.

28. A method as claimed in claim 22, wherein
the single pump stroke occurs in response to a single actuation of the piston pump.

29. A method as claimed in claim 28, wherein
fluid is driven out of the piston pump and is drawn into the piston pump during the single pump stroke.

* * * * *